United States Patent [19]

Drust

[11] Patent Number: 5,214,042
[45] Date of Patent: May 25, 1993

[54] USE OF 5-PHENYL-2-FURAN ESTERS, AMIDES AND KETONES AS NEUROPROTECTIVE AGENTS

[75] Inventor: Eugene G. Drust, Norwich, N.Y.

[73] Assignee: Norwich Eaton Pharmaceuticals, Inc., Norwich, N.Y.

[21] Appl. No.: 855,361

[22] Filed: Mar. 18, 1992

Related U.S. Application Data

[62] Division of Ser. No. 371,351, Jun. 23, 1989, Pat. No. 5,118,708.

[51] Int. Cl.⁵ .............. A61K 31/41; A61K 31/445; A61K 31/525; A61K 31/535
[52] U.S. Cl. ............................ 514/231.5; 514/251; 514/326; 514/359
[58] Field of Search ............ 514/231.5, 359, 3226, 514/251

[56] References Cited

U.S. PATENT DOCUMENTS

| | | | |
|---|---|---|---|
| 3,856,825 | 12/1974 | Wright et al. | 514/471 |
| 4,035,394 | 7/1977 | Pelosi et al. | 514/471 |
| 4,085,118 | 4/1978 | Pelosi | 514/471 |
| 4,128,550 | 12/1978 | Pelosi | 514/471 |
| 4,162,257 | 7/1979 | Pelosi et al. | 514/471 |
| 4,403,097 | 9/1983 | Pelosi et al. | 514/471 |
| 5,023,272 | 6/1991 | Burch et al. | 514/471 |
| 5,091,426 | 2/1992 | Pelosi | 514/471 |
| 5,118,708 | 6/1992 | Drust | 514/471 |

FOREIGN PATENT DOCUMENTS

271581FC2 6/1977 Fed. Rep. of Germany.

OTHER PUBLICATIONS

Chemical Abstracts 78:463, col. 1., Abs. No. 43169q (1973).

Oleinik, A. F., et al. "Synthesis and Tuberculostatic Activity of 5-Arylpyromucic Acid Derivatives", *Pharmaceutical Chemical Journal.* (English Translation) 10(4):463-465 (Apr.) 1976.

Goldenberg, M. M., "F-461, 3-Diethylamino-2,-2-Dimethylpropyl 5-(P-nitrophenyl)-2-Furoate Hydrochloride, A new Non-Anticholingergic Spasmolytic and Gastric Acid Inhibitor", *Arch. Int. Pharmacodyn. Ther.*, 222:27-39 (Jul.) 1976.

(List continued on next page.)

*Primary Examiner*—S. J. Friedman
*Attorney, Agent, or Firm*—David L. Suter; Karen F. Clark; Joanne P. Will

[57] ABSTRACT

The present invention encompasses methods of using 5-phenyl-2-furan esters, amides and ketones and compositions thereof to prevent or limit neuronal death or degeneration in a human or lower animal. These methods comprise systemically administering to such human or other animal a safe and effective amount of a compound of the formula:

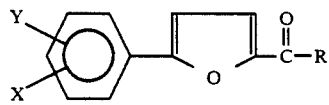

wherein
(1) X is halo or hydrogen, and Y is a substituent selected from the group consisting of unsubstituted or halogen-substituted methyl, halo, nitro, amino, and methoxy; and
(2) R is $R^1C(O)OH$, $R^1C(O)N(R^3)_2$, $N(R^3)_2$, $OR^1N(R^3)_2$, $R^1N(R^3)_2$, $N(R^2)R^1N(R^3)_2$, or $N(R^2)N(R^3)_2$; where
$R^1$ is $C_1$-$C_3$ alkyl which is unsubstituted or substituted with $C_1$-$C_2$ alkyl;
$R^2$ is hydrogen or lower alkyl; and
each $R^3$ is, independently, hydrogen or lower alkyl; or
both $R^3$ groups are connected to form a saturated 5- or 6-membered heterocycle containing 1 or 2 heteroatoms selected from oxygen and nitrogen, and said heterocycle is unsubstituted or substituted with lower alkyl or hydroxy-substituted lower alkyl;

or a pharmaceutically acceptable salt thereof.

17 Claims, No Drawings

OTHER PUBLICATIONS

Chemical Abstracts 86(19):563, col. 1., Abs. No. 86:140014h (May 9, 1977).

Burch, H. A., et al. "Phenylfurans IV: Spasmolytic 3-Diethylamino-2, 2-(dimethyl)propyl Esters of 5-Substituted Phenyl-2-furancarboxylic acids", *Jnl of Pharm. Sci.,* 69(1):107-110 (Jan. 1980).

Chemical Abstracts 96(3):432, col. 2., Abs. No. 96:19903a (Jan. 18, 1982).

Korenova, A., et al. "Ureas and amides of the 5-(2-nitrophenyl)-2-furyl type", *Chem Papers,* 42 (6):795-800(1988).

USE OF 5-PHENYL-2-FURAN ESTERS, AMIDES AND KETONES AS NEUROPROTECTIVE AGENTS

This is a divisional of application Ser. No. 07/371,351 filed on Jun. 23, 1989 now U.S. Pat. No. 5,118,708.

BACKGROUND OF THE INVENTION

This invention relates to novel use of 5phenyl-2-furan esters, amides and ketones as neuroprotective agents.

Neuronal death or degeneration occurs continually in mature mammals, including man. It can be accelerated for a variety of reasons including, but not limited to: exposure to neurotoxins, neurodegenerative diseases, trauma, and cerebrovascular accidents such as stroke.

Stroke is the most common life-threatening neurologic disease and is the third leading cause of death in the United States after heart disease and cancer. The American Heart Association estimates that there will be approximately 500,000 new victims of stroke each year.

There currently are no specific therapies to prevent or limit neuronal death or degeneration after ischemia, stroke and in neurodegenerative disorders such as Alzheimer's disease and Huntington's chorea. Accordingly, the method of this invention provides a novel therapeutic approach to prevent or limit neuronal death or degeneration. It has been discovered that 5-phenyl-2-furan esters, amides and ketones possess neuroprotective activity.

A number of phenyl furans are described in the literature. However, these compounds have never been suggested to have neuroprotective activity. For example, U. S. Pat. No. 3,856,825 issued to Wright et al. on Dec. 24, 1974, discloses a series of 3-diethylamino-2,2-dimethylpropyl 5-(substituted phenyl)-2-furoates that possess pharmacological properties, particularly being useful as antispasmodics. U. S. Pat. No. 4,162,257 issued to Pelosi and Yu on Jul. 24, 1979, discloses N,N-dimethyl-5-phenyl-2-furamides said to be useful as anti-inflammatory agents. Oleinik, A. F., "Synthesis and Tuberculostatic Activity of 5-Arylpyromucic Acid Derivatives", *Pharmaceutical Chemical Journal*, Vol. 10, No. 4 (April 1976), pages 463-465, discloses certain 5-phenyl-2-furans said to have bacteriostatic activity.

SUMMARY OF THE INVENTION

The present invention encompasses methods of using 5-phenyl-2-furan esters, amides and ketones and compositions thereof to prevent or limit neuronal death or degeneration in a human or lower animal. These methods comprise systemically administering to such human or other animal a safe and effective amount of a compound of the formula:

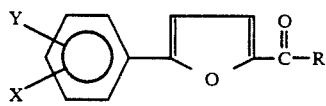

wherein (1) X is halo or hydrogen; and Y is a substituent selected from the group consisting of unsubstituted or halogen-substituted methyl, halo, nitro, amino, and methoxy; and (2) R is $R^1C(O)OH$, $R^1C(O)N(R^3)_2$, $N(R^3)_2$, $OR^1N(R^3)_2$, $R^1N(R^3)_2$, $N(R^2)R^1N(R^3)_2$, or $N(R^2)N(R^3)_2$; where $R^1$ is $C_1$-$C_3$ alkyl which is unsubstituted or substituted with $C_1$-$C_2$ alkyl;

$R^2$ is hydrogen or lower alkyl; and each $R^3$ is, independently, hydrogen or lower alkyl; or both $R^3$ groups are connected to form a saturated 5- or 6-membered heterocycle containing 1 or 2 heteroatoms selected from oxygen and nitrogen, and said heterocycle is unsubstituted or substituted with lower alkyl or hydroxy-substituted lower alkyl;

or a pharmaceutically acceptable salt thereof.

DESCRIPTION OF THE INVENTION

The present invention encompasses the method of using 5-phenyl-2-furan esters, amides and ketones for protecting neurons against neuronal death or degeneration. Specific compounds and compositions to be used in the invention must, accordingly, be pharmaceutically acceptable. As used herein, such a "pharmaceutically-acceptable" component is one that is suitable for use with humans and/or animals without undue adverse side effects commensurate with a reasonable benefit/-risk ratio.

METHODS OF TREATMENT

The present invention encompasses a method of preventing or limiting neuronal death or degeneration in a human or lower animal subject which comprises systemically administering to said human or lower animal subject a safe and effective amount of a compound (hereinafter referred to as a "5-phenyl furan") of the chemical structure:

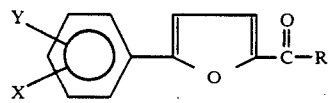

wherein (1) X is halo or nil; and Y is a substituent selected from the group consisting of unsubstituted or halogen-substituted methyl, halo, nitro, amino, and methoxy; and (2) R is $R^1C(O)OH$, $R^1C(O)N(R^3)_2$, $N(R^3)_2$, $OR^1N(R^3)_2$, $R^1N(R^3)_2$ $N(R^2)R^1N(R^3)_2$, or $N(R^2)N(R^3)_2$; where $R^1$ is $C_1$-$C_3$ alkyl which is unsubstituted or substituted with $C_1$-$C_2$ alkyl;

$R^2$ is hydrogen or lower alkyl; and each $R^3$ is, independently, hydrogen or lower alkyl; or both $R^3$ groups are connected to form a saturated 5- or 6-membered heterocycle containing 1 or 2 heteroatoms selected from oxygen and nitrogen, and said heterocycle is unsubstituted or substituted with lower alkyl or hydroxy-substituted lower alkyl;

or a pharmaceutically-acceptable salt thereof.

A "safe and effective amount" of a 5-phenyl furan is an amount that is effective to inhibit neuronal damage, death or degeneration in a human or lower animal, without undue adverse side effects commensurate with a reasonable benefit/risk ratio when used in the manner of this invention. This specific "safe and effective amount" will, obviously, vary with such factors as the particular disease, condition or circumstances which are causing the neuronal damage, death or degeneration being treated, the physical condition of the patient, the duration of treatment, the nature of concurrent therapy (if any), the specific dosage form to be used, the carrier employed, and the dosage regimen desired for the composition.

A neuroprotective agent prevents or limits neuronal death or degeneration. "Neuronal death or degeneration" may occur in pathological conditions that include, but are not limited to, stroke, hypoglycemia, transient cerebral ischemic attack, cerebral ischemia during cardiac or pulmonary surgery or cardiac arrest, perinatal asphyxia, Huntington's chorea, Alzheimer's disease, Parkinson's disease, Olivo-ponto-cerebellar atrophy, anoxia and spinal cord injury. Descriptions of these pathological conditions are found in Harrison's Principles of Internal Medicine (1987).

Stroke is a condition with sudden onset due to acute vascular lesions of the brain which is often followed by permanent neurologic damage. Hypoglycemia is a deficiency of glucose concentration in the blood which may lead to headache and sometimes convulsions. Transient cerebral attack is a temporary deficiency of blood in the cerebrum. Cerebral ischemia during cardiac pulmonary surgery or cardiac arrest is a deficiency of blood in the cerebrum. Perinatal asphyxia is an interruption of gas exchange in the lungs during the period shortly before or after birth. Alzheimer's disease is dementia of gradual onset and gradually progressive course, occurring in almost all cases after the age of fifty. Huntington's chorea is an hereditary disease marked by chronic progressive occurrence of rapid, jerky, involuntary movements and mental deterioration. Olivo-ponto-cerebellar atrophy is a wasting away of the olive, the middle peduncles and the cerebellar cortex. Parkinson's disease is characterized by stooped posture, stiffness, slowness of movement and rhythmic tremor of the limbs that subsides on active willed movement or complete relaxation.

Some 5-phenyl furans useful in these methods are described in issued U.S. Pat. Nos. and scientific literature. For example, U.S. Pat. No. 4,162,257 by Pelosi and Yu issued on Jul. 24, 1979, discloses N,N-dimethyl-5-phenyl-2-furamides that conform to the formula of the compound of this invention wherein X is nil and Y is either amino or chloro and R is N(R$^3$)$_2$, and wherein R$^3$ is methyl. The compounds of the '257 patent are said to act as anti-inflammatory agents. U.S. Pat. No. 3,856,825 by Wright et al. issued on Dec. 24, 1974, discloses a series of 3-diethyl amino-2,2-dimethylpropyl 5-(substituted phenyl)-2-furoates that conform to the formula of the compound of the present invention wherein X is nil, Y is a member of the group consisting of 4-nitro, 4-trifluoromethyl, 3,4-difluoro, 3-methoxy, 4-methyl, 4-methoxy, 4-bromo, 2,3-dichloro, 2-nitro-4-methyl, and 4-chloro; R is OR$^1$N(R$^3$)$_2$, and R$^1$ is propyl disubstituted with methyl and R$^3$ is ethyl. The compounds of the '825 patent are said to possess antispasmodic activity. "Synthesis and Tuberculostatic Activity of 5-Arylpyromucic Acid Derivatives", *Pharmaceutical Chemical Journal*, Vol. 10, No. 4 (April, 1976), by Oleinik et al. discloses 5-arylfuran-2-carboxylic acids and their derivatives. The 5-arylfuran-2-carboxylic acid hydrazides and esters are said to possess bacteriostatic activity against the tuberculosis bacillus. U.S. Pat. No. 4,162,257 and U.S. Pat. No. 3,856,825 and "Synthesis and Tuberculostatic Activity of 5-Arylpyromucic Acid Derivatives" by Oleinik et al. are incorporated by reference herein.

Preferred 5-phenyl furans useful in this method include those compounds wherein X is a para or meta substituent and is selected from the group consisting of fluoro, chloro, and bromo. Preferred 5-phenyl furans useful in this method also include those wherein Y is selected from the group consisting of halosubstituted methyl, fluoro, chloro, bromo, and methoxy. A particularly preferred 5-phenyl furan useful in this method is one wherein Y is trifluoromethyl. Preferred 5-phenyl furans useful in this method include those wherein R$^1$ is 2,2-dimethylpropyl.

Preferred compounds useful in this method include.. 3-diethylamino-2,2-dimethylpropyl 5-(p-nitrophenyl)-2-furoate hydrochloride {F-461}; 3-diethylamino-2,2-dimethylpropyl 5-(p-aminophenyl)-2-furoate dihydrochloride; 3-diethylamino-2,2-dimethylpropyl 5-(o-chlorophenyl)-2-furoate hydrochloride; 3-diethylamino-2,2-dimethylpropyl 5-(p-fluorophenyl)-2-furoate hydrochloride; 3-(diethylamino)-2,2-dimethylpropyl 5-(4-chlorophenyl)-2-furancarboxylate hydrochloride; 3-diethylamino-2,2-dimethylpropyl 5-(2,3-dichlorophenyl)-2-furoate hydrochloride; 3-diethylamino-2,2-dimethylpropyl 5-(3,4-dichlorophenyl)-2-furoate hydrochloride; 3-diethylamino-2,2-dimethylpropyl 5-(4-chloro-2-nitrophenyl)-2-furoate hydrochloride; 3-diethylamino-2,2-dimethylpropyl 5-(m-trifluoromethylphenyl)-2-furoate hydrochloride; 3-diethylamino-2,2-dimethylpropyl 5-(m-nitrophenyl)-2-furoate hydrochloride; 3-diethylamino-2,2-dimethylpropyl 5-(p-bromophenyl)-2-furoate hydrochloride; 3-diethylamino-2,2-dimethylpropyl 5-(p-methoxyphenyl)-2-furoate hydrochloride; 3-diethylamino-2,2-dimethylpropyl 5-(m-methoxyphenyl)-2-furoate fumarate; 3-diethylamino-2,2-dimethylpropyl 5-(p-trifluoromethylphenyl)-2-furoate hydrochloride; 3-diethylamino-2,2-dimethylpropyl 5-(p-methylphenyl)-2-furoate fumarate; 3-diethylamino-2,2-dimethylpropyl 5-(3,4-difluorophenyl)-2-furancarboxylate hydrochloride hemihydrate; 3-diethylamino-2,2-diethylpropyl 5-(p-nitrophenyl)-2-furoate hydrochloride; 1-methyl-4-piperidyl 5-(p-chlorophenyl)-2-furoate hydrochloride; 5-(p-chlorophenyl)-2-furamide; 5-(p-chlorophenyl)-N,N-dimethyl-2-furamide; 5-(p-chlorophenyl)-2-furoic acid 1-isopropylhydrazide; 5-(4-aminophenyl)-N-[2-(diethylamine)ethyl]-2-furancarboxamide hydrochloride; 5-(4-bromophenyl)-N-[3-(4-morpholinel)propyl]-2-furancarboxamide hydrate; N-[3-(diethylamino)-2,2-dimethylpropyl]-5-(4-trifluoromethylpenyl)-pb 2-furancarboxamide (Z)-2-butenedioic acid salt; 5-(2,4-dichlorophenyl)-N-[3-(4-morpholinyl)propyl]-2-furancarboxamide hydrochloride hydrate; 1-[5-(4-nitrophenyl)-2-furanylcarbonyl]piperazine hydrobromide; 3-dimethylamino-1-(5-phenyl-2-furanyl)-1-propanone hydrochloride tetartohydrate; 3-dimethylamino-1-[5-(4-chlorophenyl)-2-furanyl]-1-propanone hydrochloride; 3-dimethylamino-1-[5-(4-methoxyphenyl)-2-furanyl]-1-propanone hydrochloride; 1-[5-(4-chlorophenyl)-2-furanyl]-3-[1-(4-methylpiperazinyl)]-1propanone dihydrochloride hemihydrate; 1-(5-(2-nitrophenyl)-2-furanyl]-3-(I-piperidinyl)-1-propanone hydrochloride; 3-[5-(4-chlorophenyl)-2-furanyl]-3-oxopropanamide; 1-[5-(4-chlorophenyl)-2-furanyl]-3-(1-pyrrolidinyl)-1-propanone hydrochloride; 1-[5-(4-chlorophenyl)-2-furanyl]-3-(1-piperidinyl)-1-propanone hydrochloride; 1-[5-(3,4-dichlorophenyl)-2-furanyl]-3-(1-piperidinyl)-1-propane hydrochloride; 1-[5-(4-fluorophenyl)-2-furanyl]-3-(1-piperidinyl)-1-propanone hydrochloride; 1-[5-(3-chlorophenyl)-2-furanyl]-3-(1-piperidinyl)-1- propanone hydrochloride; 1-[5-(4-bromophenyl)-2-furanyl]-3-(1-piperidinyl)-1-propanone hydrochloride; 1-[5-(4-chlorophenyl)-2-furanyl]-3-[1-(3-methylpiperidinyl)]-1propanone hydrochloride; 1-[5-(4-chlorophenyl)-2-furanyl]-3-[1-(3-hydroxymethylpiperidinyl)]-1-propanone hydrochloride; 1-[5-(4-chlorophenyl)-2-furanyl]-2-(diethylamino)ethanone hydrochloride; 3-diethylamino-]-[5-(p-chlorophenyl)-2-furyl]-1.propanone hydrochloride.

More preferred 5-phenyl furans useful in this method include: 3-diethylamino-2,2-dimethylpropyl 5-(p-nitrophenyl)-2-furoate hydrochloride; 3-diethylamino-2,2-dimethylpropyl 5-(p-fluorophenyl)-2-furoate hydrochloride; 3-(diethylamino)-2,2-dimethylpropyl 5-(4-chlorophenyl)-2-furancarboxylate hydrochloride; 3-diethylamino-2,2-dimethylpropyl 5-(3,4-dichlorophenyl)-2-furoate hydrochloride; 3-diethylamino-2,2-dimethylpropyl 5-(4-chloro-2-nitrophenyl)-2-furoate hydrochloride; 3-diethylamino-2,2-dimethylpropyl 5-(m-trifluoromethylphenyl)-2-furoate hydrochloride; 3-diethylamino-2,2-dimethylpropyl 5-(m-nitrophenyl)-2-furoate hydrochloride; 3-diethylamino-2,2-dimethylpropyl 5-(p-bromophenyl)-2-furoate hydrochloride; 3-diethylamino-2,2-dimethylpropyl 5-(p-methoxyphenyl)-2-furoate hydrochloride; 3-diethylamino-2,2-dimethylpropyl 5-(m-methoxyphenyl)-2-furoate fumarate; 3-diethylamino-2,2-dimethylpropyl 5-(p-trifluoromethylphenyl)-2-furoate hydrochloride; 3-diethylamino-2,2-dimethylpropyl 5-(p-methylphenyl)-2-furoate fumarate; 3-diethylamino-2,2-dimethylpropyl 5-(3,4-difluorophenyl)-2-furancarboxylate hydrochloride hemihydrate; 1-methyl-4-piperidyl 5-(p-chlorophenyl)-2-furoate hydrochloride; 5-(p-chlorophenyl)-2-furamide; 5-(p-chlorophenyl)-N,N-dimethyl-2-furamide; 5-(p-chlorophenyl)-2-furoic acid 1-isopropylhydrazide; 5-(4-aminophenyl)-N-[2-(diethylamino)ethyl]-2-furancarboxamide hydrochloride; 5-(4-bromophenyl)-N-[3-(4-morpholinyl)propyl]-2-furancarboxamide hydrate; 5-(2,4-dichlorophenyl)-N-[3-(4-morpholinyl)propyl]-2-furancarboxyamide hydrochloride hydrate; 1-[5-(4-nitrophenyl)-2-furanylcarbonyl]piperazine hydrobromide; 3-dimethylamino-1-(5-phenyl-2-furanyl)-1-propanone hydrochloride tetartohydrate; 3-dimethylamino-1-[5-(4-chlorophenyl)-2-furanyl]-1-propanone hydrochloride; 3-dimethylamino-1-[5-(4-methoxyphenyl)-2-furanyl]-1-propanone hydrochloride; 1-[5-(4-chlorophenyl)-2-furanyl]-3-[1-(4-methylpiperazinyl)]-1propanone dihydrochloride hemihydrate; 1-[5-(2-nitrophenyl)-2-furanyl]-3-(1-piperidinyl)-1-propanone hydrochloride; 3-[5-(4-chlorophenyl)-2-furanyl]-3-oxopropanamide; N-[3-(diethylamino)-2,2-dimethylpropyl]-5-(4-trifluoromethylpenyl)-2-furancarboxamide (Z)-2-butenedioic acid salt; 1-[5-(4-chlorophenyl)-2-furanyl]-3-(1-pyrrolidinyl)-1-propanone hydrochloride; 1-[5-(4-chlorophenyl)-2-furanyl]-3-(1-piperidinyl)-1-propanone hydrochloride; 1-[5-(3,4-dichlorophenyl)-2-furanyl]-3-(1-piperidinyl)-1propanone hydrochloride; 1-[5-(4-fluorophenyl)-2-furanyl]-3-(1-piperidinyl)-1-propanone hydrochloride; 1-[5-(3-chlorophenyl)-2-furanyl]-3-(1-piperidinyl)-1-propanone hydrochloride; 1-[5-(4-bromophenyl)-2-furanyl]-3-(1-piperidinyl)-1-propanone hydrochloride; 1-[5-(4-chlorophenyl)-2-furanyl]-3-[1-(3-methylpiperidinyl)]-1propanone hydrochloride; 1-[5-(4-chlorophenyl)-2-furanyl]-3-[1-(3-hydroxymethylpiperidinyl)]-1-propanone hydrochloride; 1-[5-(4-chlorophenyl)-2-furanyl]-2-(diethylamino)ethanone hydrochloride; 3-diethylamino-1-[5-(p-chlorophenyl)-2-furyl]-1-propanone hydrochloride.

Particularly preferred is 3-diethylamino-2,2-dimethylpropyl 5-(p-trifluoromethylphenyl)-2-furoate hydrochloride.

As used herein, the number 2 and number 6 labeled position on the phenyl group are collectively referred to as the "ortho" or "o" position; the number 5 and number 3 labeled position are collectively referred to as the "meta" or "m" position; and the number 4 labeled position is referred to as the "para" or "p" position.

The compounds of this invention are readily prepared by methods well-known in the chemical literature. Preferably a substituted 5-phenyl-2-furoyl chloride is reacted with an appropriately substituted alcohol or amine in the presence of a solvent such as toluene to prepare the 5-phenyl-2-furyl-esters and 5-phenyl-2-furyl amides, respectively. It is preferred to prepare the 5-phenyl-2-furyl ketones by reaction of a substituted 5-phenyl-2-furyl methyl ketone with the appropriate amine and paraformaldehyde in the presence of hydrochloric acid and a solvent such as butanol. Amino substituted compounds are prepared by reduction of the nitro to the amino groups in the presence of palladium-on-charcoal and a solvent such as alcohol.

EXAMPLE I 3-Diethylamino-2,2-dimethylpropyl 5-(p-Fluorophenyl)-2-furoate Hydrochloride

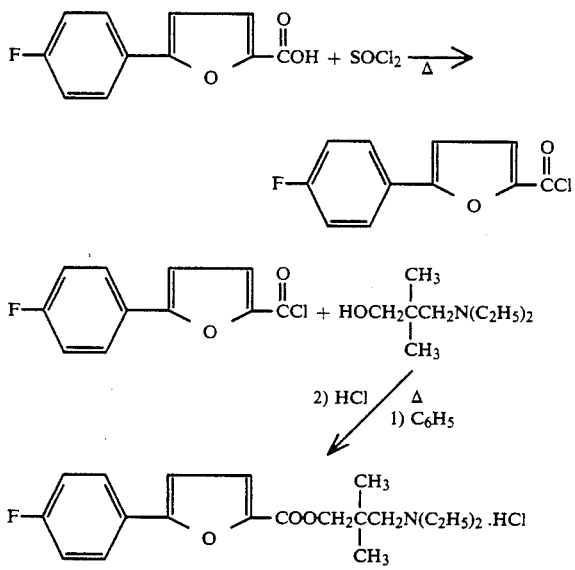

5-(p-Fluorophenyl)-2-furoic acid (18.6 g., 0.09 mole) is added with rapid stirring to thionyl chloride (31.5 ml.) at room temperature, heated until solution occurs about ¼ hr.) and then is refluxed for 2 hr. The mixture is stirpped of excess thionyl chloride in vacuo, benzen (100 ml.) is added, and again stripped of solvent. The residue is treated with a solution of 3-diethylamino-2,2-dimethylpropyl (14.5 g. 0.09 mole) in benzene (490 ml.), is refluxed for 3 hr., cooled, is diluted with petroleum ether (300 ml.), and is stored for 2 days at room temperature. The benzene- petroleum ether solution is decanted, the residue dissolved in $H_2O$ (750 ml.) and the solution adjusted to pH 8 with saturated aqueous $Na_2CO_3$ (75 ml.). The product is extracted from the aqueous phase with benzene (860 ml.) in portions and the extract dried for 18 hours over $MgSO_4$ and activated charcoal.

The solution is filtered and the filtrate adjusted to pH 3 with ether-HCl (cooled in ice bath). Petroleum ether (400 ml.) is added and the product oiled out of solution. The benzene-petroleum ether solution is decanted and the product washed twice with anhydrous ether (scratching induced crystallization). The solid is recrystallized from isopropanol (200 ml.) to yield 16.9 g. (49%). A sample is recrystallized from isopropanol, m.p. 134°-138°.

One hundred milligrams of the above compound is administered to a human suffering a stroke to limit neuronal death or degeneration.

EXAMPLE II 3-Diethylamino-2,2-dimethylpropyl 5-(p-Chlorophenyl)-2-furoate Hydrochloride

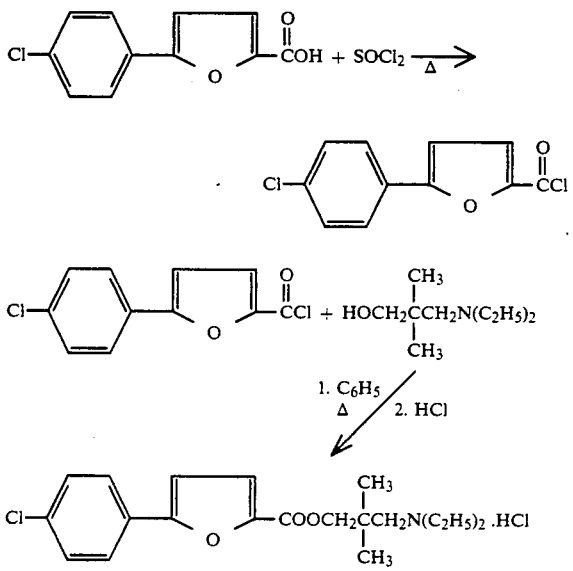

5-(p-Chlorophenyl)-2-furoic acid (33.5 g., 0.15 mole) is added with rapid stirring to thionyl chloride (58 ml.) at room temperature, heated until solution occurs ( about 20 min.) and then refluxed for 2 hr. The mixture is tripped of excess thionyl chloride in vacuo, benzene (100 ml.) is added, and against stripped of solvent. The residue is treated with a solution of 3-diethylamino-2,2-dimethylpropyl (24.1 g., 0.15 mole) in benzene (700 ml.), refluxed for 4 hr., cooled, diluted with petroleum ether (450 ml.) and stored for 18 hours at room temperature. The benzene-petroleum ether solution is decanted, the residue is dissolved in H$_2$O (1000 ml.), and the solution is adjusted to pH 8 with saturated aqueous Na$_2$CO$_3$(70 ml.). The product is extracted from the aqueous phase with benzene (1000 ml.) in portions and the extract is dried overnight with MgSO$_4$ and activated charcoal. The solution is filtered and the filtrate is adjusted to pH 3 with ether-HCl (cooled in ice bath). Petroleum ether (300 ml.) is added and the product oiled out of solution. The benzene-petroleum ether solution is decanted and the product is washed twice with anhydrous ether (scratching induced crystallization). The solid is recrystallized from ethanol (200 ml.) to yield: 32 g. (53%). A sample is recrystallized twice from isopropanol, m.p. 139°-143°.

Fifty milligrams of the above compound is administered to a human subject suffering from cardiac arrest to limit neuronal degeneration.

EXAMPLE III 3-Diethylamino-2,2-diethylpropyl 5-(p-Nitrophenyl)-2-furoate Hydrochloride

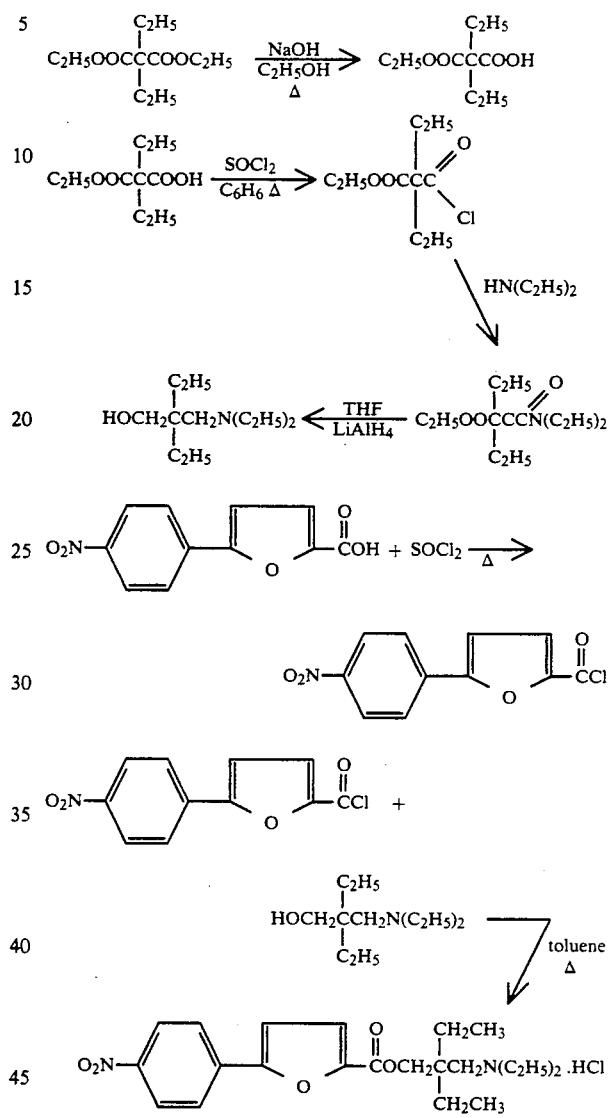

Monoethyl Diethylmalonate

A mixture of diethyl diethylmalonate (43 g., 0.20 mole) in absolute ethanol (300 ml.) and N° OH (10 g., 0.25 mole) is refluxed for 0.5 hour. The reaction mixture is stored at room temperature for 2 days, filtered to remove insoluble solid, and the filtrate is concentrated to dryness under reduced pressure at 70°-75° bath. The oily residue is dissolved in H$_2$O (50 ml.), acidified to a pH of 2-3 10% HCl with cooling, and is extracted with ether (240 ml.). The ether extract is dried over MgSO4, is filtered, and is concentrated to dryness under reduced pressure at 50°-70° bath, to yield 37 g (98%) of monoethyl diethylmalonate.

Ethyl 2-(N,N-Diethylcarbamoyl)-2-ethylbutyrate

To a solution of monoethyl diethylmalonate (28 g. 0.15 mole) in dry benzene (300 ml.) is added SOCl$_2$ (15 ml., 0.21 mole) at 26°-28° in 2 min, with mechanical stirring. The reaction solution is gradually heated to 78° over 25 min, then is heated an additional 45 min at 85°-90°. The mixture is concentrated to dryness under reduced pressure, benzene (100 ml.) is added, and the mixture is again concentrated to dryness. The resultant oily residue dissolved in benzene (200 ml ) is treated dropwise with a solution of diethylamine (30 ml., 0.z9 mole) in benzene (90 ml.) at 5°-15° over 17 min, and the reaction mixture is refluxed for 7 hours. The mixture is stored for 18 hours at room temperature and is filtered (to remove insoluble salt), is washed with benzene (50 ml.), is dried over $MgSO_4$ and activated charcoal for 15 min, is filtered, and is concentrated to dryness under reduced pressure (bath at 50°-60°). This will yield 29 g. (79%) of ethyl 2-(N,N-diethylcarbamoyl)-2-ethylbutyrate.

3-Diethylamino-2.2-diethylpropanol

To THF (300 ml.) is added $LiAlH_4$ (1.2 g), the mixture is refluxed for 20 min, and an additional quantity of $LiAlH_4$ (15.8 g., 0.42 mole) is added in two portions at 5°-21° over 1 min with mechanical stirring. The mixture is cooled to 5° and a solution of ethyl 2-(N,N-diethylcarbamoyl)-2-ethylbutyrate (29 g., 0.12 mole) in THF (80 ml.) is added at 5°-11° in 5 min. The temperature (exothermic) is allowed to rise to 60 over 12 min, is maintained at 49°-53° for 7 min, is heated gradually to reflux over 10 min, and then is refluxed for 6 hours. After it stands at room temperature for 18 hours, the reaction mixture is treated with $Ac_2O$ (55 ml.) at 10°-20°, is stirred in an ice bath for 0.5 hour, is treated with $H_2O$ (150 ml.) at 10°-18°, and finally is treated with $CHCl_3$ (250 ml.) at 10°-22° with slow stirring. The $CHCl_3$-layer is washed with $H_2O$ (50 ml.), is dried over $MgSO_4$, is filtered, and is concentrated to dryness under reduced pressure. The resultant oil (30 ml.) is treated with 10% HCl (280 ml.) and is subjected to steam distillation for 1.3 hours, collecting 1 liter of distillate. The distillate is concentrated to 50 ml. by distillation under reduced pressure, is made basic with solid $NaC_2O_3$ to pH 8-9 in the cold, is extracted with ether, is dried over $MgSO_4$ and activated charcoal, is filtered, and concentrated to dryness. The residual oil (12 g. plus 5.0 g. from previous run) is distilled at 60°-68°/1 mm to yield 11 g (35%) of 3-diethylamino-2,2-diethylpropanol.

3-Diethylamino-2,2-diethylpropyl 5-(p-nitrophenyl)-2-furoate Hydrochloride 5-(p-Nitrophenyl)-2-furoic acid (13.7 g., 0.059 mole) is added with rapid stirring to thionyl chloride (34 ml.), is heated until solution occurs, and is refluxed for 3 hrs. The mixture is stripped of excess thionyl chloride under reduced pressure. Benzene (100 ml.) is added, and the mixture is again stripped of solvent. The residue is trealed with a solution of 3-diethylamino-2,2-diethylpropanol (11 g., 0.059 mole) in toluene (150 ml.), is refluxed for 3 hrs, cooled, is diluted with petroleum ether (150 ml.) and is stored for 18 hours at room temperature. The product is collected by filtration and is recrystallized from isopropanol, to yield 16 g (62%) of 3-diethylamino-2,2-diethylpropanol 5-(p-nitrophenyl)-2-furoate hydrochloride. A sample is recrystallized from isopropanol, m.p. 152°-156°.

One hundred milligrams of the above compound is administered to a human experiencing acute cerebral ischemia.

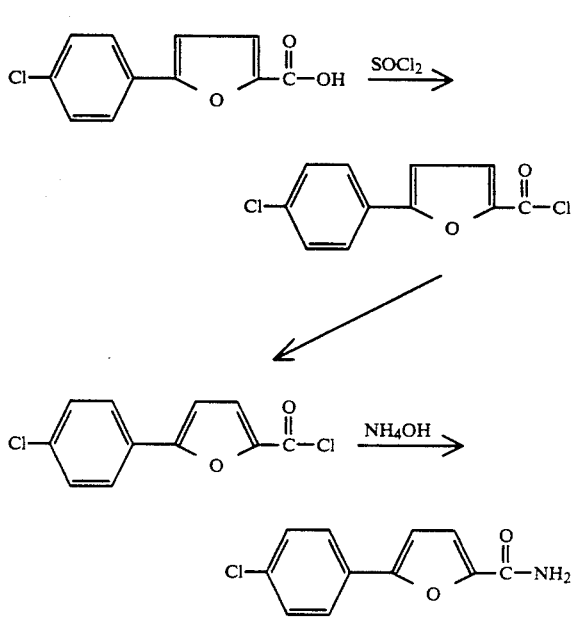

A mixture Of 56 g. (0.25 mole) Of 5-(p-Chlorophenyl)-2furoic acid and 100 ml. of $SOCl_2$ is refluxed for 3½ hours so that HCl gas evolves and there is dissolution. The $SOCl_2$ is removed on a rotary evaporator. Benzene is added to the solid residue and is then removed on the rotary evaporator to give 5-(p-chlorophenyl)-2-furoyl chloride To 1000 ml. of cold, stirring $NH_4OH$, 63 g. (0.26 mole) of 5-(p-chlorophenyl)-2-furoyl chloride is added portionwise. The resulting mixture is stirred at once bath temperature for 15 minutes and then is stored at room temperature for 18 hours. The solid is filtered, is washed with water and is dried at 60° to yield 56 g. (97%).

Fifty milligrams of the above compound is administered to a human suffering from cerebral ischemia during cardiac arrest to limit neuronal death.

1-[5-(4-Nitrophenyl)-2-furanylcarbonyl]piperazine Hydrobromide

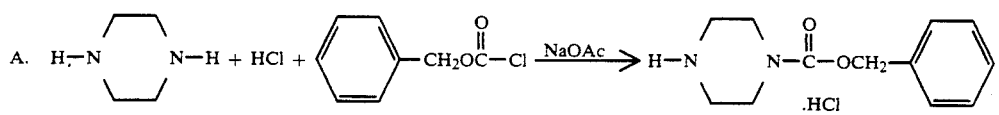

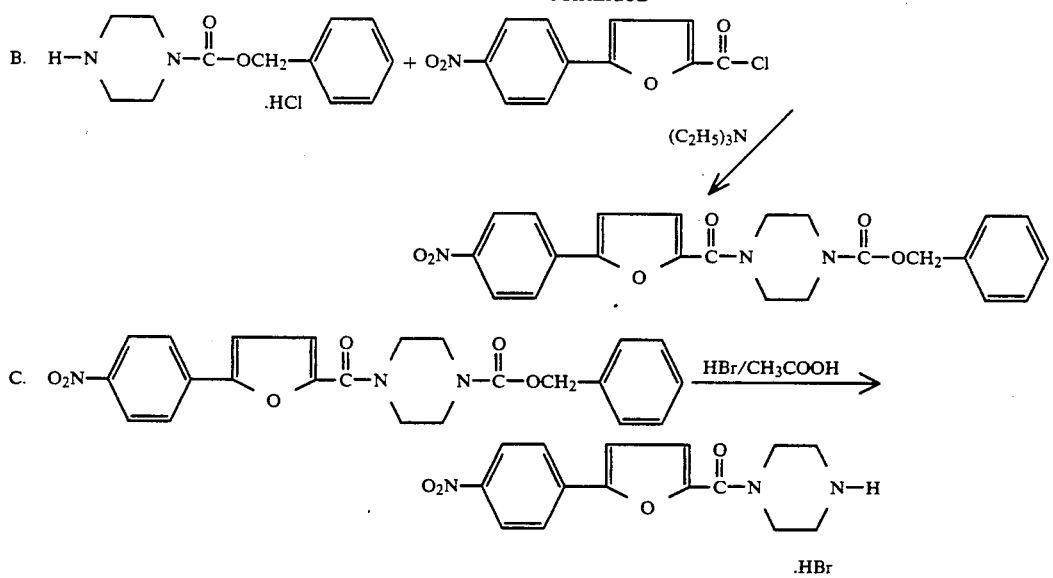

A. Preparation of Phenylmethyl 1-piperazincecarboxylate Hydrochloride

A solution of 47 g. (0.55 mole) of anhydrous piperazine in 550 ml. of H₂O is adjusted to a pH of 2 by the portionwise addition of 95 ml. of concentrated hydrochloric acid. Acetone (550 ml.) is added. A few drops from a solution of 118 g. of anhydrous NaOAc in 300 ml. of H₂O is added to adjust the pH to 3. Carbenzoxy chloride (100 g., 0.590 mole) is added simultaneously to the remaining sodium acetate solution. The sodium acetate solution is added by means of a PH stat with the pH of the reactions being kept between 3 to 3.2. The reaction is stirred at ambient temperature for 4 hr. The reaction mixture is set for vacuum distillation with the volume of the reaction being reduced by two-thirds. The resulting solid (1,4-bis[(phenylmethoxy)carbonyl ]) is filtered and is set aside. The filtrate is taken to dryness on a rotary evaporator to yield a white solid. This solid is extracted with 3×500 ml. portions of refluxing ethanol. The combined extracts are concentrated on a rotary evaporator to yield a residual solld. This solid is washed in hexane and is air dried to yield 104 g. (73%) of preparation of phenylmethyl 1-piperazinecarboxylate hydrochloride.

B. 4-[5-(4-Nitrophenyl)-2-furanylcarbonyl]-1-(phenylmethoxycarbonyl) piperazine An 8 g (0.03 mole) sample of Phenylmethyl 1-piperazinecarboxylate hydrochloride is dissolved in a minimal amount of H₂O and is made strongly basic with 3N N° OH solution. This resulting mixture is extracted with ether. The ether is dried over MgSO₄ and the solvent is then removed on ° rotary evaporator to yield the free base as a residual oil. This oil, 3.5 g. (0.035 mole) of triethylamine, and 75 ml. of tollene is heated to 80°. At a temperature of 75°-80° a warm solution of 8 g. (0.03 mole) of 5-(4-nitrophenyl)-2-furoyl chloride in 150 ml. of toluene is added dropwise. The resulting mixture is heated for 3 hr. at steam bath temperature and then is allowed to cool to room temperature. A small amount of sollid is filtered and discarded. The filtrate is taken to dryness on a rotary evaporator to yield a residual oil. This oil is triturated in ethyl acetate with a solid forming. The solid is filtered and is air dried to yield 10 5 g. (80%) of 4-[5-(4-Nitrophenyl)-2-furanylcarbonyl]-1(phenylmethoxycarbonyl) piperazine.

C. 1-]5-(4-Nitrophenyl}-2-furanylcarbonyl]piperazine Hydrobromide

To a 20 g. (0.46 mole) sample of the above compound is added 400 ml. of a saturated solution of HBr/CH₃COOH. The resulting solution is slowly warmed to 40° with a precipitate forming. Stir this mixture at 40°-45° for 30 min, stir at ambient temperature for 30 min and then cool in an ice bath. The solid is filtered and then is stirred 1n refluxing methanol. The mixture is cooled and then is filtered. The solid is dried in a desiccator over NaOH to yield 17 g. (97%).

One hundred milligrams of the a[ove compound is administered to a human suffering from perinatal asphyxia to limit neuronal death.

EXAMPLE VI
N-[3-(4-Morpholinyl)propanyl]-5-(4-bromoohenvl)-2-furancarboxamide

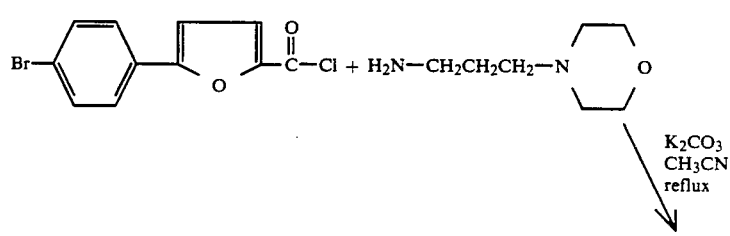

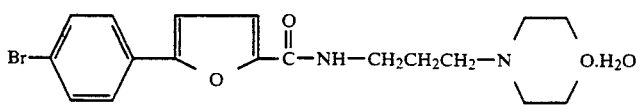

A mixture of 4.06 g of 5-(4-bromphenyl)-2-furancarboxylic acid chloride and 2.55 g of N-(3-aminopropyl)-morpholine is refluxed 6 hr with 3.0 g of anhydrous potassium carbonate in 50 ml of acetonitrile. The mixture is allowed to stir at room temperature overnight. Solvents are then evaporated and the residue is triturated with ethyl ether followed by evaporation again. This process is repeated several times. A solution of the residue in ethyl ether is allowed to stand overnight whereupon crystals are formed. After three recrystallizations from ethyl acetate, the product, 2.47 g (37.5%), melts at 83°-100°. The CI and EI mass spec. are consistent with the proposed structure. The latter showed $M+ = 393$.

Fifty milligrams of the above compound is administered to a human afflicted with Huntington's chorea to limit neuronal degeneration.

EXAMPLE VII
N-[3-(4-Morpholinyl)propyl]-5-(2,4-dichlorophenyl)-2-furancarboxamide Hydrochloride Hydrate tallized from absolute ethanol. Five additional recrystallizations are required to obtain the desired product which weighs 6:370 g (13.5%); m.p. 201°-204°.

One hundred milligrams of the above compound is administered to a human afflicted with Parkinson's disease to limit neuronal degeneration.

EXAMPLE VIII

A human subject afflicted with Alzheimer's disease is given 25 mg of 3-diethylamino-2,2-dimethylpropyl 5-(3-trifluoromethylphenyl-(2-furoate hydrochloride (from U. S. Pat. No. 3,856,825) three times per day. The administration of 3-diethylamino-2,2-dimethylpropyl 5-(3-trifluoromethylphenyl)-2-furoate hydrochloride limits neuronal degeneration. This therapy extends for the lifetime of the human subject. In the above example, 3-diethylamino-2,2-dimethylpropyl 5-nitrophenyl)-2-furoate hydrochloride; 3-diethylamino-2,2-dimethylpropyl 5-(3,4-dichlorophenyl)-2-furoate hydrochloride; 3-diethylamino-2,2-dimethylpropyl 5-(4-chloro-2- -nitrophenyl)-2-furoate hydrochloride; 3-diethylamino-

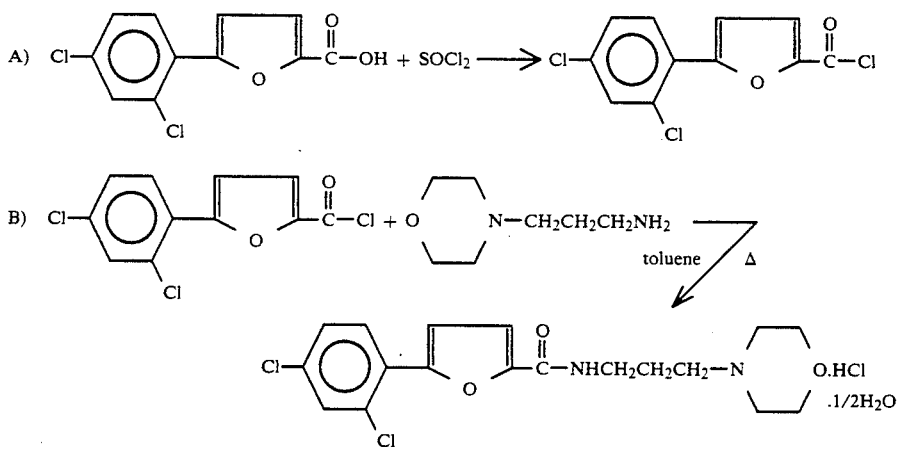

A) Preparation of 5-(2,4-Dichlorophenyl)-2-furanoyl Chloride

A solution of 28.28 g (0.11 moles) of 5-(2,4-dichlorophenyl)-2-furancarboxylic acid in 43 ml of thionyl chloride is heated at reflux of 3 hours. The solvent is removed and the residue is treated with 100 ml of toluene. the solvent is removed and the residue is carried on directly to the next step of the reaction.

B) Preparation of N-3-(4-Morpholinyl)propyll-5-(2.4-dichloroohenyl)-2-furancarboxamide Hydrochloride Hydrate A solution of 15.86 g (0.11 mole) of N-(3-aminopropyl)-morpholine and the above prepared residue in 600 ml of toluene is heated at reflux for 3 hours and is then allowed to stand at room temperature overnight. Petroleum ether (400 ml) is added to the reaction mixture and is then allowed to stand at room temperature overnight. A solid is filtered and dissolved in 600 ml of isopropanol followed by adding 1-liter of ethyl ether. Upon cooling a solid forms which is filtered and recrys- 2,2-dimethylpropyl 5-(m-trifluorumethylphenyl)-2-furoate hydrochloride; 3-diethylamino-2,2-dimethylpropyl 5-(m-nitrophenyl)-2-furoate hydrochloride; 3-diethylamino-2,2-dimethylpropyl 5-(p-bromophenyl)-2-furoate hydrochloride; 3-diethylamino-2,2-dimethylpropyl 5-(p-methoxyphenyl)-2-furoate hydrochloride; 3-diethylamino-2,2-dimethylpropyl 5-(m-methoxyphenyl)-2-furoate fumarate; 3-diethylamino-2,2-dimethylpropyl 5-(p-methylphenyl)-2-furoate fumarate (P-768); 3-diethylamino-2,2-dimethylpropyl 5-(3,4-difluorophenyl)-2-furancarboxylate hydrochloride hemihydrate; methyl-4-piperidyl 5-(p-chlorophenyl)-2-furoate hydrochloride; 5-(p-chlorophenyl)-N,N-dimethyl-2-furamide; 5-(p-chlorophenyl)-2-furoic acid 1-isopropylhydrazide; 5-(4-aminophenyl)-N-[2-(diethylaminu)ethyl]-2-furancarboxamine hydrochloride; 5-(4-bromophenyl)-N-[3-(4-morpholinyl)propyl]-2-furancarboxamide hydrate; N-[3-diethylamino)-2,2-dimethylpropyl]-5-(4-trifluoromethyl-phenyl)-1-furancarboxamide (Z)-2-butenedioic acid salt; 5-(2,4- dichlorophenyl)-N-[3-(4-morpholinyl)propyl]-2-furan-carboxamide hydrochloride hydrate; are substituted for 3-diethylamino-2,2-dimethylpropyl 5-(3-trifluoromethyl phenyl)-2furoate hydrochloride with substantially similar results.

EXAMPLE IX
3-Dimethylamino-1-[5-(4-chlorophenyl)-2-furanyl]-1-propanone Hydrochloride

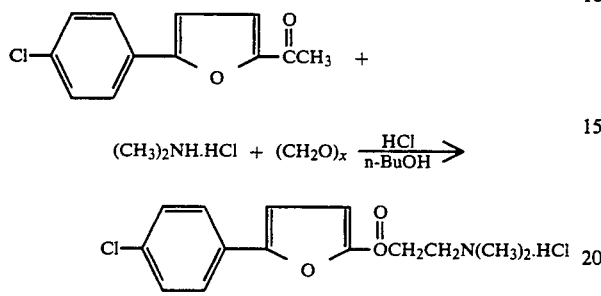

A solution of 22 g. (0.10 mole) of 5-(p-chlorophenyl)-2-furyl methyl ketone, 16 g. (0 20 mole) of dimethylamine hydrochloride, 6 g (0.20 mole) of Paraformaldehyde, 100 ml. of n-butanol, and 1 ml. of concentrated HCl is heated under reflux for 2 hr. Solvent is removed on a rotary evaporator and the yellow, residual solid is partitioned between ether and water. The layers are separated and the water layer is washed with ether. The water layer is made basic with 1N NaOH solution and is extracted twice with ether. The ethereal layers are dried over MgSO₄ and are concentrated on a rotary evaporator to give a residual semi-solid. The solid is dissolved in 350 ml. of isopropanol and is treated with ethereal HCl. The solid which is deposited is collected by filtration and is dried in a 60° oven . to give 13 g (42%) of product.

Fifty milligrams of the above compound is administered to a human suffering from Olivo-ponto-cerebellar atrophy to limit neuronal degeneration.

EXAMPLE X
1-[2-5-(2-Nitrophenyl)-2-furanylcarbonyl]ethyl]piperidine Hydrochloride

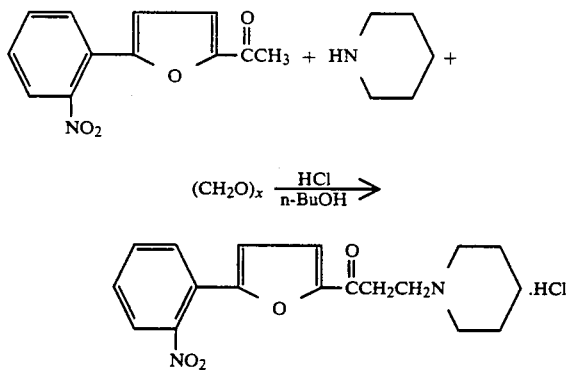

Concentrated HCl (16 ml.) is added to a stirred solution of 17 g. (0.20 mole) of piperidine in 100 ml. of n-butanol. To this solution is added 23 g. (0.10 mole) of 5-(o-nitrophenyl)-2-furyl methyl ketone and 6.0 g. (0.20 mole) of paraformaldehyde. The solution is heated under reflux for 3 hr. and the solvent is removed on a rotary evaporator. The residual semi-solid is partitioned between ether and water, the layers are separated, and the ether layer is dried over MgSP₄. The solvent is removed on a rotary evaporator to give a residual oil. The oil is dissolved in anhydrous ether and is treated with ethereal HCl. The solid is collected by filtration and is dissolved in 300 ml. of CH₃CN. The solution is concentrated and cooled in ice to give solid which is collected by filtration. Recrystallization from CH₃CN and then recrystallization with absolute ethanol-anhydrous ether mixture gives 6.5 g. (28%) of Product, m.p. 160°–162°.

One hundred milligrams of the above compound is administered to a human suffering from anoxia to limit neuronal degeneration.

EXAMPLE XI
3-[5-(4-Chlorophenyl)-2-furanyl]-3-oxopropanamide

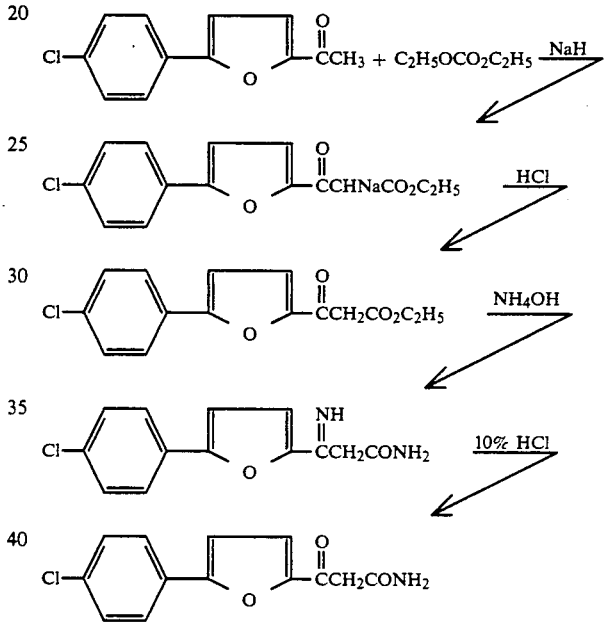

To a stirring solution of 2000 ml. of diethyl carbonate in an ice bath is added portionwise 78 g (1.94 mole) of NaH. While maintaining ice bath temperature, 213g (0.97 mole) of 5-(p-chlorophenyl)-2-furyl methyl Ketone is added portionwise. The bath is removed and the reaction is stirred at ambient temperature for one hour and the refluxed for 4 hrs. An additional 1000 ml. of diethyl carbonate is added to aid in stirring. The mixture is cooled and 130 ml. of ethanol is added dropwise. The solid is filtered, is washed with hexane and is air-dried to yield 225 g. (74%) of ethyl 3-[5-(4-chlorophenyl)-2-furanyl]-3-oxopropanate.

A 50 g. (0.16 mole) sample of ethyl 3-[5-(4-chlorophenyl)-2furanyl]-3-oxopropanate Na salt is suspended in a mixture of 500 ml. of ether and 500 ml. of H₂O. The resulting mixture is acidified with concentrated hydrochloric acid. The ether layer is then separated, dried over MgSO₄ and concentrated on a rotary evaporator to yield a residual oil. This oil is extracted with refluxing hexane and the hexane upon cooling yields 12.5 g (27%) of product. An analytical sample is prepared by recrystallizing a sample from hexane and drying in the vacuum pistol at room temperature, m.p. 46°-47°.

A pressure vessel charged with 2 g. (0.0068 mole) of ethyl 3-[5-(4-chlorophenyl)-2-furonyl]-3-oxopropanate and 50 ml. of concentrated NH₄OH is heated in a boiling water bath for 6½ hours. The resulting mixture is allowed to stand in the pressure vessel at room temperature for 18 hours. The solid is filtered, and then recrystallized with activated charcoal from ethyl acetate and dried in the vacuum p.stoll at room temperature to yield 0.5 g (28%), m.p. 212°-214°.

A mixture of 1.7 g (0.0065 moie) of 3-[5-(4-chlorophenyl)- 2-furanyl]-3-iminopropanamide and 20 ml. of 10% hydrochloric acid is warmed on a steam bath with dissolution. A solid forms after 15 minutes of heating. This solid is filtered, recrystallized with activated charcoal from nitromethane, and dried for 4 days in the vacuum pistol at the temperature of boiling water to yield 1.0 g (59%) of product, m.p. 180°-181°.

Fifty milligrams of the above compound is administered to a human who has suffered a spinal c rd injury to limit neuronal degeneration.

EXAMPLE XII

A human subject who experiences global cerebral ischemia during cardiac surgery is administered 100 mg of 3-diethylamino-2,2-dimethylpropyl 5-(p-trifluoromethylphenyl)-2-furoate hydrochloride intravenously, preventing significant brain injury.

EXAMPLE XIII

A human subject afflicted with Alzheimer's disease is given 100 mg of 3-dimethylamino-1-[5-(4-chlorophenyl)-2-furanyl]-1-propanone hydrochloride twice a day limiting or preventing the progression of the disease. This is chronic therapy for the rest of the human subject's life.

EXAMPLE XIV

A person diagnosed as having Huntington's chorea is given 200 mg of 1-[5-(4-chlorophenyl)-2-turanyl]-3-[1-(4-methylpiperazinyl)]-1-propanone dihydrochloride hemihydrate three times a day before or Just at the time of onset of symptoms of Huntington's chorea. Administration of this compound limits the progression of the symptoms of Huntington's chorea.

EXAMPLE XV

A human subject who has experienced a brain injury is given 100 mg of N-(3-diethylamino-2,2-dimethylpropyl)-5-(p-chlorophenyl)-2-furamide hydrochloride four times a day for up to ten days after the trauma that caused the brain injury. Administration of this compound prevents the secondary death of neurons that follows the primary death of neurons caused by the trauma.

EXAMPLE XVI

A human subject who has experienced a stroke is given 50 mg of 3-diethylamino-2,2-dimethylpropyl 5-(p-trifluoromethylphenyl)-2-furoate hydrochloride twice a day for up to fourteen days after the incidence of stroke. Administration of this compound prevents or limits the death of neuruns.

What is claimed is:

1. A method of limiting neuronal death or degeneration in a human or lower animal subject, comprising systemically administering to said subject a safe and effective amount of a compound of the formula;

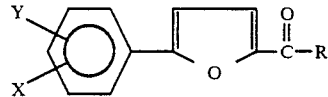

wherein:
(a) X is halo or hydrogen, Y is a substituent selected from the group consisting of unsubstituted or halogen-substituted methyl, halo, nitro, amino, and methoxy; and
(b) R is $R^1C(O)N(R^3)_2$, $N(R^2)_2$, $OR^1N(R^3)_2$, $R^1N(R^3)_2$, $N(R^2)R^1N(R^3)_2$, or $N(R^2)N(R^3)_2$; where
$R^1$ is $C_1$-$C_3$ alkyl which is unsubstituted or substituted with $C_1$-$C_2$ alkyl;
$R^2$ is hydrogen or lower alkyl; and both $R^3$ groups are connected to form a saturated 5- or 6-membered heterocycle containing 1 or 2 heteroatoms selected from oxygen and nitrogen and said heterocycle is unsubstituted or substituted with lower alkyl or hydroxy-substituted lower alkyl; or a pharmaceutically acceptable salt of ester thereof.

2. A method of limiting neuronal death or degeneration in a human or lower animal subject, according to claim 1 wherein X is hydrogen.

3. A method of limiting neuronal death or degeneration in a human or lower animal subject, according to claim 1 wherein X is halo.

4. A method of limiting neuronal death or degeneration in a human or lower animal subject, according to claim 1 wherein Y is halosubstituted methyl.

5. A method of limiting neuronal death or degeneration in a human or lower animal subject, according to claim 1 wherein Y is trifluoromethyl.

6. A method of limiting neuronal death or degeneration in a human or lower animal subject, according to claim 1 wherein R is or $R^1C(O)N(R^3)_2$.

7. A method of limiting neuronal death or degeneration in a human or lower animal subject, according to claim wherein R is $N(R^3)_2$, $N(R^2)R^1N(R^3)_2$ or $N(R^2)N(R^3)_2$.

8. A method of limiting neuronal death or degeneration in a human or lower animal subject, according to claim 1 wherein R is $OR^1N(R^3)_2$.

9. A method of limiting neuronal death or degeneration in a human or lower animal subject, according to claim 2 wherein R is 3-diethylamino-2,2-dimethylpropyl and Y is selected from the group consisting of: para- and meta-fluoro, para- and meta-chloro, para- and meta-trifluoromethyl, meta-nitro, para- and meta-bromo, para- and meta-methoxy, para-methyl, para-amino and ortho-chloro.

10. A method of limiting neuronal death or degeneration in a human or lower animal subject, according to claim 3 wherein R is 3-diethylamino-2,2-dimethylpropyl and X and Y are the same substituent selected from the group consisting of chloro and fluoro.

11. A method of limiting neuronal death or degeneration in a human or lower animal subject, according to claim 9 wherein Y is selected from the group consisting of: para- and meta-fluoro, para- and meta-chloro, para- and meta-triflouromethyl, meta-nitro, para- and meta-bromo, para- and meta-methoxy, and para-methyl.

12. A method of limiting neuronal death or degeneration in a human or lower animal subject, comprising systemically administering to said subject a safe and effective amount of 3-diethylamino-2,2-dimethylpropyl 5-(p-trifluoromethylphenyl)-2-furoate hydrochloride.

13. A method of limiting neuronal death or degeneration in a human or lower animal subject according to claim 1 wherein said subject is afflicted with a disorder selected from the group consisting of: stroke, hypoglycemia, transient cerebral ischemic attack, cerebral ischemia during cardiac or pulmonary surgery or cardiac arrest, perinatal asphyxia, Huntington's chorea, Alzheimer's disease, Parkinson's disease, Olivo-ponto-cerebellar atrophy, anoxia and spinal cord injury.

14. A method of limiting neuronal death or degeneration in a human or lower animal subject, according to claim 13, wherein said subject is afflicted with a stroke.

15. A method of limiting neuronal death or degeneration in a human or lower animal subject, according to claim 13, wherein said subject is afflicted with Alzheimer's disease.

16. A method of limiting neuronal death or degeneration in a human or lower animal subject, according to claim 13, wherein said subject is afflicted with cerebral ischemia during cardiac or pulmonary surgery or cardiac arrest.

17. A method of limiting neuronal death or degeneration in a human or lower animal subject, according to claim 13, comprising systemically administering to said subject a safe and effective amount of 3-diethylamino-2,2-dimethylpropyl 5-(p-trifluoromethylphenyl)-2-furoate hydrochloride.

* * * * *